(12) United States Patent
Choi et al.

(10) Patent No.: US 11,786,669 B2
(45) Date of Patent: Oct. 17, 2023

(54) MEDICINE INJECTION DEVICE

(71) Applicant: PHILOSYS CO., LTD., Gunsan-si (KR)

(72) Inventors: Woo Hyek Choi, Yongin-si (KR); Jeong Sik Kim, Seoul (KR); Seung Won Lee, Seoul (KR); Young Min Park, Seoul (KR)

( * ) Notice: Subject to any disclaimer, the term of this patent is extended or adjusted under 35 U.S.C. 154(b) by 557 days.

(21) Appl. No.: 17/005,251

(22) Filed: Aug. 27, 2020

(65) Prior Publication Data

US 2021/0060261 A1 Mar. 4, 2021

(30) Foreign Application Priority Data

Aug. 30, 2019 (KR) .......................... 10-2019-107391

(51) Int. Cl.
*A61M 5/315* (2006.01)
(52) U.S. Cl.
CPC .... *A61M 5/31581* (2013.01); *A61M 5/31501* (2013.01); *A61M 5/31528* (2013.01); *A61M 5/31566* (2013.01); *A61M 5/31575* (2013.01); *A61M 5/31583* (2013.01); A61M 2205/8262 (2013.01)
(58) Field of Classification Search
CPC .......... A61M 5/31581; A61M 5/31585; A61M 5/31578; A61M 5/31501; A61M 5/31566; A61M 5/20; A61M 5/3157; A61M 5/31528; A61M 5/31588; A61M 5/31583; A61M 5/31575; A61M 5/31568; A61M 5/24; A61M 5/31576; A61M 2005/31588; A51M 5/31513
See application file for complete search history.

(56) References Cited

U.S. PATENT DOCUMENTS

2007/0233001 A1 * 10/2007 Burroughs .............. A61M 5/20
604/131

* cited by examiner

*Primary Examiner* — Laura A Bouchelle
(74) *Attorney, Agent, or Firm* — ANTONIO HA & U.S. PATENT, LLC

(57) ABSTRACT

According to an embodiment, a cartridge driving module comprises a motor and a shaft extending along a rotational axis of the motor, a power transmission screwed to the shaft and moving forward when the shaft rotates in a forward direction and moving back when the shaft rotates in a backward direction, a pusher connected to the power transmission and exerting a pressure to a medicine cartridge containing a medicine when the power transmission moves forward, and a position maintaining unit exerting an external force to the power transmission in a direction along which the power transmission moves forward, when the power transmission moves back up to a predetermined stop position.

9 Claims, 13 Drawing Sheets

MEDICINE INJECTION DEVICE

CROSS-REFERENCE TO RELATED APPLICATION(S)

This application is based on and claims priority under 35 U.S.C. 119 to Korean Patent Application No. 10-2019-0107391, filed on Aug. 30, 2019, in the Korean Intellectual Property Office, the disclosure of which is herein incorporated by reference in its entirety.

TECHNICAL FIELD

Embodiments of the disclosure relate to medicine injection devices.

DESCRIPTION OF RELATED ART

Conventionally, insulin-dependent patients measure blood sugar on an empty stomach, after lunch, before or after dinner, and before sleep using a self-blood sugar tester.

When blood sugar control is needed, the patient determines and injects an appropriate amount of insulin on her own using an insulin syringe.

Such blood sugar management requires a self-blood sugar tester, insulin cartridge, or insulin injection device.

The patient accurately records the measured glucose level and the amount of insulin injected and shows the record to a specialist to receive feedback.

For example, an insulin-dependent patient can check the current blood sugar level through a self-measurement device by dropping blood collected by piercing the skin through a lancet and dropping it on a test strip.

When blood sugar control is determined to be necessary, the patient may use an insulin injector.

The patient manually sets the amount of insulin recommended by her doctor on the insulin injector.

The patient places the insulin injector on the skin to be injected and manually injects the insulin.

The patient herself is required to record the measured blood glucose level and the injected amount.

SUMMARY

According to an embodiment, there is provided a cartridge driving module that may prevent locking due to over-engagement during operation and a medicine injection device including the cartridge driving module.

According to an embodiment, there are provided a cartridge driving module that is easy to return to a preset position for replacing the medicine cartridge and a medicine injection device including the cartridge driving module.

According to an embodiment, a cartridge driving module comprises a motor and a shaft extending along a rotational axis of the motor, a power transmission screwed to the shaft and moving forward when the shaft rotates in a forward direction and moving back when the shaft rotates in a backward direction, a pusher connected to the power transmission and exerting a pressure to a medicine cartridge containing a medicine when the power transmission moves forward, and a position maintaining unit exerting an external force to the power transmission in a direction along which the power transmission moves forward, when the power transmission moves back up to a predetermined stop position.

A first thread may be formed on an outer surface of the shaft. The power transmission may include an insertion hole through which the shaft may be inserted. A second thread may be formed on an inner circumferential surface of the insertion hole. The first thread may be engaged with the second thread.

In the direction along which the power transmission moves forward, the shaft may include a first portion having a circular cross section and a second portion extending from an end of the first portion. The first thread may be formed on an outer surface of the second portion.

In the direction along which the power transmission moves forward, the insertion hole may include a first insertion portion having a cross section corresponding to the shaft and having the second thread formed on an inner circumferential surface thereof and a second insertion portion communicating with the first insertion portion and having a larger cross section than the first insertion portion.

Transmission of a rotational force from the shaft may be cut off when the second portion of the shaft may be positioned at the second insertion portion of the insertion hole while the power transmission moves back.

The predetermined stop position may be a position where the first portion of the shaft is inserted into the first insertion portion of the insertion hole.

When the power transmission moves back and arrives at the predetermined stop position, the position maintaining unit exerts an external force in the direction along which the power transmission moves forward to thereby keep the power transmission in position.

The position maintaining unit may include an elastic member wound around the first portion of the shaft and compressed by the power transmission to exert an elastic force to the power transmission.

According to an embodiment, a medicine injection device comprises a motor and a shaft connected with the motor, a medicine cartridge containing a medicine and, when pressed, discharging the medicine to an outside, a pusher connected with the medicine cartridge to apply a pressure to the medicine cartridge, and a power transmission connecting the shaft and the pusher. The power transmission moves forward in a direction of the medicine cartridge when the shaft rotates in a first direction and moves back in a direction of the motor when the shaft rotates in a second direction opposite to the first direction. The shaft and the power transmission are screwed with each other not to be locked.

The shaft may include a first thread formed on an outer surface thereof. The power transmission may include an insertion hole through which the shaft is inserted and a second thread formed on an inner circumferential surface of the insertion hole and engaged with the first thread. The first thread and the second thread have the same pitch and different thread angles. The shaft may include a plurality of protruding surfaces protruding outward along a circumference thereof and a plurality of recessed surfaces depressed inward as viewed in a cross section view perpendicular to a length direction of the shaft.

The medicine injection device may comprise a position maintaining unit maintaining the power transmission in a predetermined stop position while the power transmission moves back. The position maintaining unit may include an elastic member disposed between the motor and the power transmission.

When the engagement between the power transmission and the shaft may be released when the power transmission arrives at the predetermined stop position.

According to an embodiment, a cartridge driving module and a medicine injection device including the cartridge driving module may prevent locking due to inter-thread engagement to thereby prolong its lifespan.

According to an embodiment, a cartridge driving module and a medicine injection device including the cartridge driving module allow for easier replacement of the medicine cartridge.

According to an embodiment, the disclosure is not limited to the foregoing effects and other various effects may be apparent to one of ordinary skill in the art from the following description of embodiments.

BRIEF DESCRIPTION OF THE DRAWINGS

A more complete appreciation of the disclosure and many of the attendant aspects thereof will be readily obtained as the same becomes better understood by reference to the following detailed description when considered in connection with the accompanying drawings, wherein.

DETAILED DESCRIPTION

Hereinafter, embodiments of the disclosure are described in detail with reference to the accompanying drawings.

The same or substantially the same reference denotations are used to refer to the same or substantially the same elements throughout the specification and the drawings.

When determined to make the subject matter of the disclosure unclear, the detailed description of the known configurations or functions may be skipped.

Such denotations as "first," "second," "A," "B," "(a)," and "(b)," may be used in describing the components of the disclosure.

These denotations are provided merely to distinguish a component from another, and the essence of the components is not limited by the denotations in light of order or sequence.

When a component is described as "connected," "coupled," or "linked" to another component, the component may be directly connected or linked to the other component, but it should also be appreciated that other components may be "connected," "coupled," or "linked" between the components.

The same reference denotations may be used to refer to the same or substantially the same elements throughout the specification and the drawings.

Unless stated otherwise, the description of any one embodiment may be applied to other embodiments of the disclosure, and no repetitive or duplicate description is given of the same or substantially the same elements or features.

Figure 1:
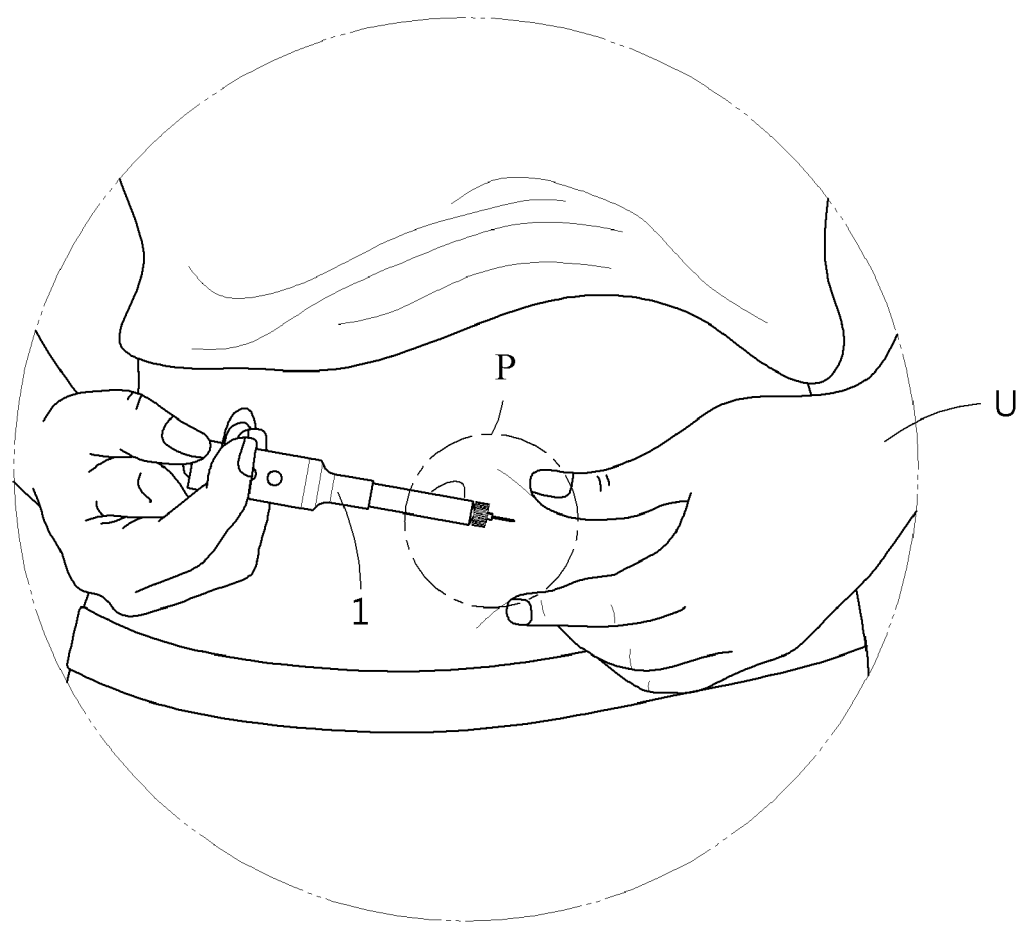
FIG. 1 is a view illustrating an example of using a medicine injection device according to an embodiment.

FIG. 1 is a view illustrating an example of using a medicine injection device according to an embodiment.

Referring to FIG. 1, according to an embodiment, a medicine injection device 1 may be used to sense or obtain information about a biological material in the user U's body and to inject a medicine into the user U's body.

The medicine injection device 1 may be used in an invasive manner in which the medicine injection device 1 penetrates the skin of the user U and is inserted into the body.

Hereinafter, the skin area of the user U where the medicine injection device 1 is inserted is referred to as an "invasion site P."

The medicine injection device may be inserted into the invasion site P and sense biological material information in the body of the user U.

The biological material may be a substance contained in the body fluids of the user U.

For example, the medicine injection device 1 may detect glucose from the body fluids of the user U and sense blood glucose concentration information for the user U.

The medicine injection device 1 may inject a target medicine into the body of the user U according to the detected biological material information.

For example, when the biological material information is blood glucose concentration, the target medicine injected by the medicine injection device 1 may be insulin that reduces the blood glucose concentration.

Figure 2:
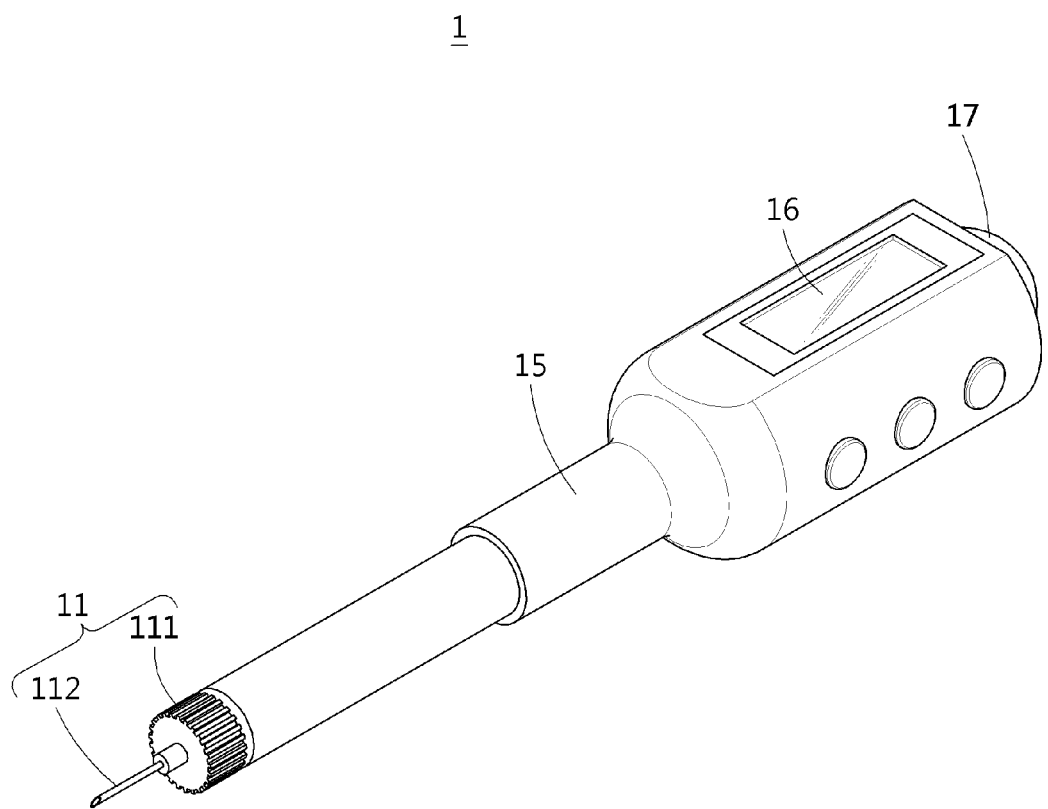
FIG. 2 is a perspective view illustrating a medicine injection device according to an embodiment.
Figure 3:
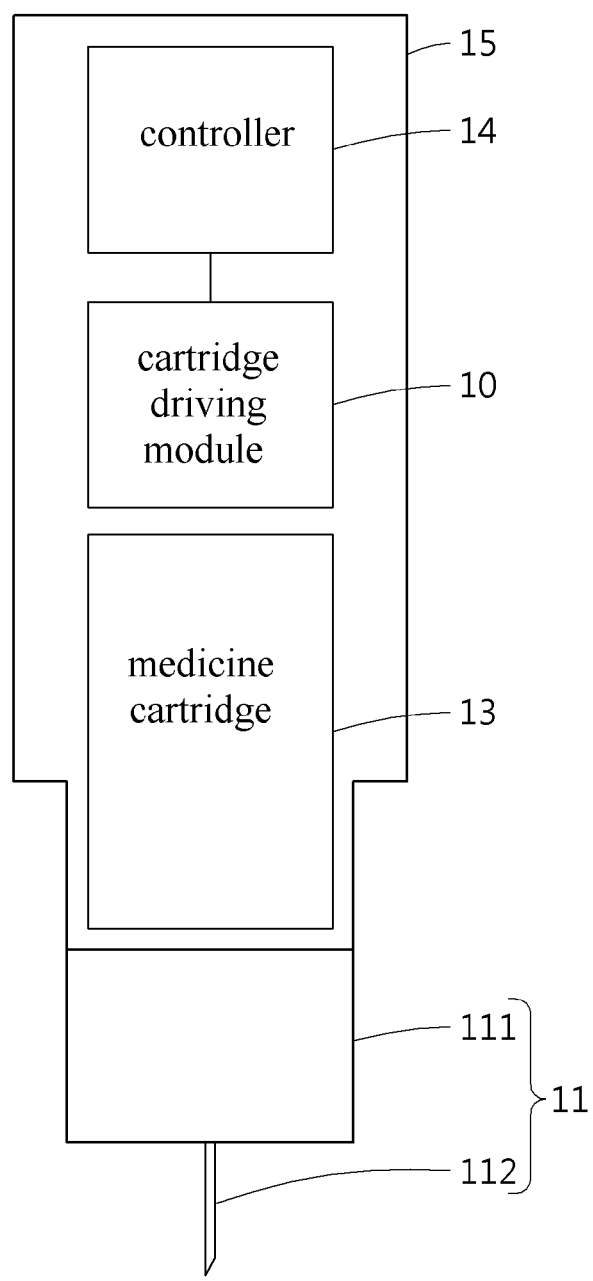
FIG. 3 is a view illustrating a configuration of a medicine injection device according to an embodiment.

FIG. 2 is a perspective view illustrating a medicine injection device according to an embodiment. FIG. 3 is a view illustrating a configuration of a medicine injection device according to an embodiment.

Referring to FIGS. 2 and 3, according to an embodiment, the medicine injection device 1 may include a needle head 11, a body housing 15, a display 16, an operation unit 17, a medicine cartridge 13, a cartridge driving module 10, an analyzer (not shown), and a controller 14. The needle head 11 may be inserted into the invasion site.

The needle head 11 may be inserted into the body of the user U and discharge the medicine through the invasion site to the body of the user U.

The needle head 11 may be detachably coupled to the body housing 15.

For example, the needle head 11 may be selectively coupled to the body housing 15 and be replaced or exchanged depending on its use.

However, this is merely an example. For example, the needle head 11 may be integrated with the body housing 15.

For ease of description, an example is described below in which the needle head 11 is detachably coupled with the body housing 15.

The needle head 11 may include a support 111 connected to the body housing 15 and a needle 112 projecting from the support 111 in the lengthwise direction thereof.

The support 111 may support the needle 112.

The support 111 may be detachably coupled to the body housing 15.

For example, the body housing 15 and the support 111 may be formed in a structure of being coupled together.

The body housing 15 and the support 111, respectively, may include connectors (not shown) electrically connected with each other to allow the body housing 15 and the support 111 to be electrically connected with each other in their coupled state.

By connection via the connectors, the needle head 11 may transfer recognition information to an inner component of the body housing 15 or receive operation signals from the inner component of the body housing 15.

The needle 112 may be directly inserted into the body of the user U.

The needle 112 may project from the support 111 in the lengthwise direction thereof and may have a sharp tip to penetrate the skin of the user U.

The needle 112 may include a hollow passing through the inside thereof along the length direction.

The medicine in a medicine cartridge 13 may be injected into the body of the user U through the hollow.

By the structure of the medicine injection device 1, the needle head 11 may be removed from the body housing 15 and be replaced when the life of the needle head 11 is over, e.g., when the use of the needle head 11 is ended.

Because of being inserted into the body of the user for use, the needle head 11 may be replaced for sanitary purposes.

As such, the needle head 11 is easily replaceable, so that easier maintenance and long-term use are possible for the medicine injection device 1.

The body housing 15 may form the outer look or appearance of the medicine injection device 1.

The body housing 15 may receive components for operating the medicine injection device 1 and support the components in place.

The body housing 15 may have a shape to allow the user U to grip easily or conveniently. For example, the body housing 15 may be shaped as a pen as shown in FIG. 2.

However, the shape of the body housing 15 shown is merely an example and is not limited thereto.

The display 16 is disposed on an outer surface of the body housing 15 and may display information about the medicine injection device 1 to the user U.

For example, the display 16 may display information related to the operation of the medicine injection device 1.

The display 16 may display biometric or biological information and medicine injection information as various pieces of visual information, such as text, symbols, or graphs.

The operation unit 17 may be disposed on an outer surface of the body housing 15 and be manipulated, controlled, or operated by the user U.

The operation unit 17 may be operated by the control action of the user U and transfer operation information to the controller 14.

The medicine cartridge 13 may contain a medicine.

The medicine cartridge 13 is replaceably inserted into the inside of the body housing 15, and an end of the medicine cartridge 13 may be connected to the needle head 11.

The medicine cartridge 13 may be connected to a cartridge driving module 10 and, as the cartridge driving module 10 operates, the medicine cartridge 13 may receive a pressure or be pressurized.

The medicine cartridge 13 may include an outlet in an end thereof.

When the medicine cartridge 13 is pressurized or receives a pressure, the medicine may be discharged through the outlet from the medicine cartridge 13.

The medicine discharged out of the medicine cartridge 13 may be injected through the hollow of the needle 112 to the inside of the body, e.g., the invasion site, of the user U.

The cartridge driving module 10 may apply a pressure to the medicine cartridge 13 to allow the medicine to be discharged out of the medicine cartridge 13.

The cartridge driving module 10 may be connected with the medicine cartridge 13 and apply an external force to a side of the medicine cartridge 13 to discharge the medicine from the medicine cartridge 13 to the needle head 11.

The analyzer may analyze the medicine injection information about the medicine injection device 1.

The analyzer may analyze the amount of the medicine remaining in the medicine cartridge 13 according to the amount of the medicine injected to the user's body.

The analyzer may be connected with the medicine cartridge 13 and analyze the amount of medicine injected to the user's body based on the information about the amount of medicine discharged from the medicine cartridge 13.

The controller 14 may control the operation of the medicine injection device 1.

The controller 14 may control the operation of the cartridge driving module 10 according to the amount of medicine determined by the analyzer, thereby adjusting the amount of medicine discharged from the medicine cartridge 13 to the needle head 11.

Figure 4:
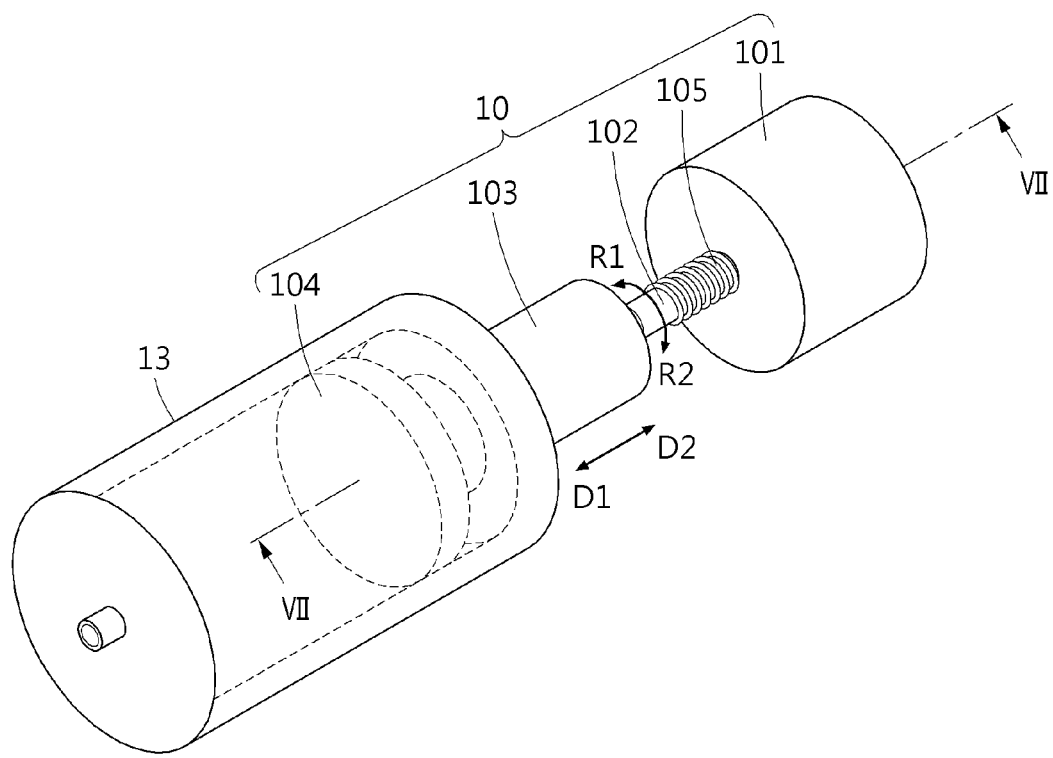
FIG. 4 is a perspective view illustrating a cartridge driving module according to an embodiment.
Figure 5:
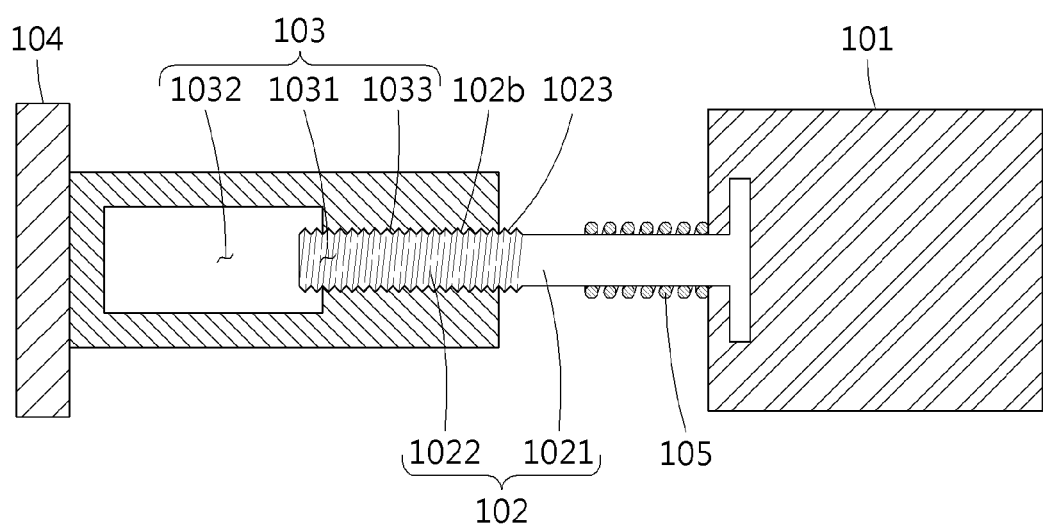
FIG. 5 is a cross-sectional view taken along line VII-VII of FIG. 4, according to an embodiment.

FIG. 4 is a perspective view illustrating a cartridge driving module according to an embodiment. FIG. 5 is a cross-sectional view taken along line VII-VII of FIG. 4.

Referring to FIGS. 4 and 5, the cartridge driving module 10 may be connected with the medicine cartridge 13.

The cartridge driving module 10 may apply a pressure to the medicine cartridge 13 to discharge the medicine out of the medicine cartridge 13.

The cartridge driving module 10 may include a motor 101, a shaft 102, a power transmission 103, a pusher 104, and a position maintaining unit 105.

The motor 101 may receive power and operate.

The shaft 102 may extend from the motor 101 along the rotational axis and may rotate as the motor 101 operates.

The rotational direction of the shaft 102 may be adjusted according to the operation of the motor 101.

For example, the shaft 102 may be rotated clockwise or counterclockwise around the rotational axis thereof or the motor 101.

The power transmission 103 may be screwed to the shaft 102.

The power transmission 103 may extend along the length direction of the shaft 102 and be translated in the length direction thereof as the shaft 102 rotates.

The moving direction of the power transmission 103 may be determined depending on the rotational direction of the shaft 102.

For example, as the shaft 102 rotates in the forward direction R1, the power transmission 103 may move in a direction D1 receding from the shaft 102 and, as the shaft 102 rotates in the backward direction R2, the power transmission 103 may move in a direction D1 approaching the shaft 102.

Hereinafter, for ease of description, the movement of the power transmission 103 when the shaft 102 rotates in the forward direction R1 is referred to as 'forward movement,' and the movement of the power transmission 103 when the shaft 102 rotates in the backward direction R2 is referred to as 'backward movement.'

The shaft 102 and the power transmission 103 may be screwed to each other.

For example, a first thread 1023 may be formed on the outer surface of the shaft 102, and a second thread 1033 may be formed on the power transmission 103 to be engaged with the first thread 1023.

The power transmission 103 may include an insertion hole formed along the length direction thereof to allow the shaft 102 to be inserted thereto.

A second thread 1033 may be formed on the inner circumferential surface of the insertion hole to be engaged with the first thread 1023.

Along the forward direction D1 of the power transmission 103, the shaft 102 may include a first portion 1021 having a circular cross section and a second portion 1022 extending from an end of the first portion 1021 and having the first thread 1023 formed on the outer surface thereof.

For example, the outer circumferential surface of the first portion 1021, positioned adjacent to the motor 101, may be unthreaded, and the second portion 1022 extending from the first portion 1021 may be threaded, i.e., have the first thread 1023 formed therein.

Along the forward direction D1 of the power transmission 103, the insertion hole of the power transmission 103 may include a first insertion portion 1031 and a second insertion portion 1032 communicating with the first insertion portion 1031.

The shaft 102 may be inserted into the first insertion hole 1031 before being inserted into the second insertion hole 1032, and the second thread 1033 may be formed on the inner circumferential surface of the first insertion portion 1031.

The second insertion portion 1032 may communicate with the first insertion portion 1031 and may have a larger cross section than the first insertion portion 1031.

Thus, when the shaft 102 is inserted to the second insertion portion 1032, the inner circumferential surface of the second insertion portion 1032 and the outer surface of the shaft 102 may be prevented from contacting each other.

By such a structure, the shaft 102 and the power transmission 103 may be connected to each other to receive the power from the motor 101 only within a predetermined range.

In other words, while the power transmission 103 is translated as the shaft 102 rotates and reaches a predetermined position, the transfer of power between the shaft 102 and the power transmission 103 may be cut off.

For example, when the power transmission 103 arrives at a predetermined stop position while moving backward, the transfer of power from the shaft 102 may be cut off.

For example, the stop position may be a position where the first portion 1021 is inserted into the first insertion portion 1031 of the insertion hole.

For example, the shaft 102 enters the second portion 1022 past the first portion 1021 of the insertion hole. When the second portion 1022 of the shaft 102, having the first thread 1023 formed therein, fully enters the second portion 1022 past the first portion 1021 of the insertion hole, the engagement between the first thread 1023 and the second thread 1033 may be released so that the transfer of power between the power transmission 103 and the shaft 102 may be cut off.

For example, when the second portion 1022 of the shaft 102 fully passes through the first insertion portion 1031 of the insertion hole and is positioned in the second insertion portion 1032, the first portion 1021 of the shaft 102 is positioned in the first insertion portion 1031 of the insertion hole and, thus, the first thread 1023 and the second thread 1033 depart off, or are disengaged from, each other so that the transmission of the rotational force of the shaft 102 to the power transmission 103 may be cut off.

Since the cartridge driving module 10 applies a pressure to the medicine cartridge 13 via the forward movement of the power transmission 103, if the medicine cartridge 13 is replaced, the power transmission 103 may need to return to its initial position via its backward movement.

In the case where the power transmission 103 is moved backward by the rotational force of the motor 101, if the power transmission 103 is moved back beyond the predetermined stop position due to excessive rotation of the motor 101, the power transmission 103 and the shaft 102 may be over-engaged, so that locking may occur. As a result, the coupling between the medicine cartridge 13 and the cartridge driving module 10 may be released.

According to an embodiment, by the structure of the cartridge driving module 10, the backward movement of the power transmission 103 is limited to the predetermined stop position, so that locking or decoupling may be prevented.

The pusher 104 may connect the power transmission 103 and the medicine cartridge 13.

The pusher 104 may be connected to an end of the power transmission 103 and, as the power transmission 103 moves forward, directly applies a pressure to the medicine cartridge 13, allowing the medicine to be discharged out of the medicine cartridge 13.

For example, the pusher 104 may be inserted inside the medicine cartridge 13.

Thus, by the forward movement of the power transmission 103, the medicine cartridge 13 may discharge the medicine through the outlet by the same principle of a syringe.

The pusher 104 may seal off the connection sites to prevent leakage of the medicine from the medicine cartridge 13 while moving inside the medicine cartridge 13.

For example, the pusher 104 may include a compressible elastic material.

The position maintaining unit 105 may apply an external force to the power transmission 103 in order to move the power transmission 103 forward.

The position maintaining unit 105 may apply an external force to the power transmission 103 in the direction along which the power transmission 103 moves forward, when the power transmission 103 is moved back up to the predetermined stop position.

The position maintaining unit 105 may be, or include, an elastic member wound around the first portion 1021 of the shaft 102. For example, the position maintaining unit 105 may be, or include, a spring.

As the power transmission 103 moves back, the elastic member may be compressed by the power transmission 103 and exert an elastic force to the power transmission 103 in the direction of the forward movement of the power transmission 103.

By the structure, the position maintaining unit 105 may keep the power transmission 103 in the predetermined stop position while the power transmission 103 moves back.

The power transmission 103 is moved back up to the predetermined stop position by the rotation of the shaft 102. When the power transmission 103 reaches the predetermined stop position, the transmission of power from the shaft 102 may be cut off.

In this case, the power transmission 103 may be continuously moved back by the inertia even though the transmission of power is cut off. The position maintaining unit 105 may press the power transmission 103 in the direction of forward movement, thereby keeping the power transmission 103 in the predetermined stop position.

The first thread 1023 of the shaft 102 and the second thread 1033 of the power transmission 103 are disengaged from each other in the predetermined stop position. Thus, the first thread 1023 and the second thread 1033 need to be engaged with each other for the power transmission 103 to move forward in the stop position.

In such a case, the position maintaining unit 105 presses the power transmission 103 in the direction of forward movement, assisting in engagement between the first thread 1023 and the second thread 1033 by the rotation of the shaft 102.

Figure 6:
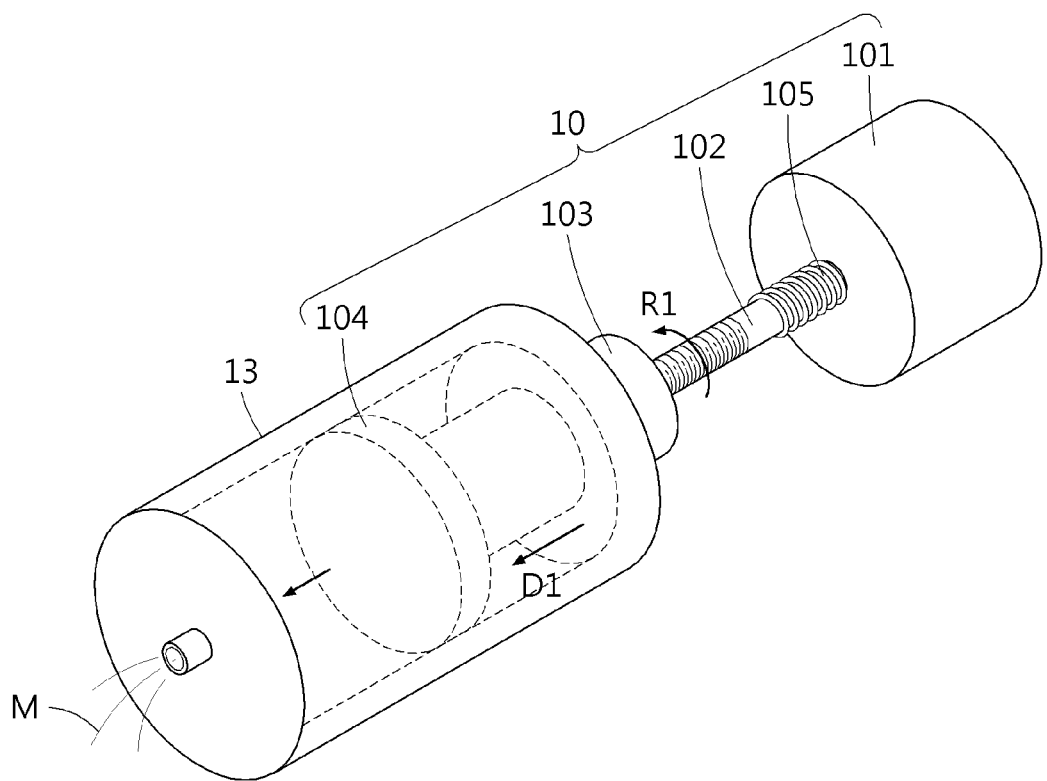
FIG. 6 is a view illustrating an example operation of a cartridge driving module according to an embodiment.
Figure 7:
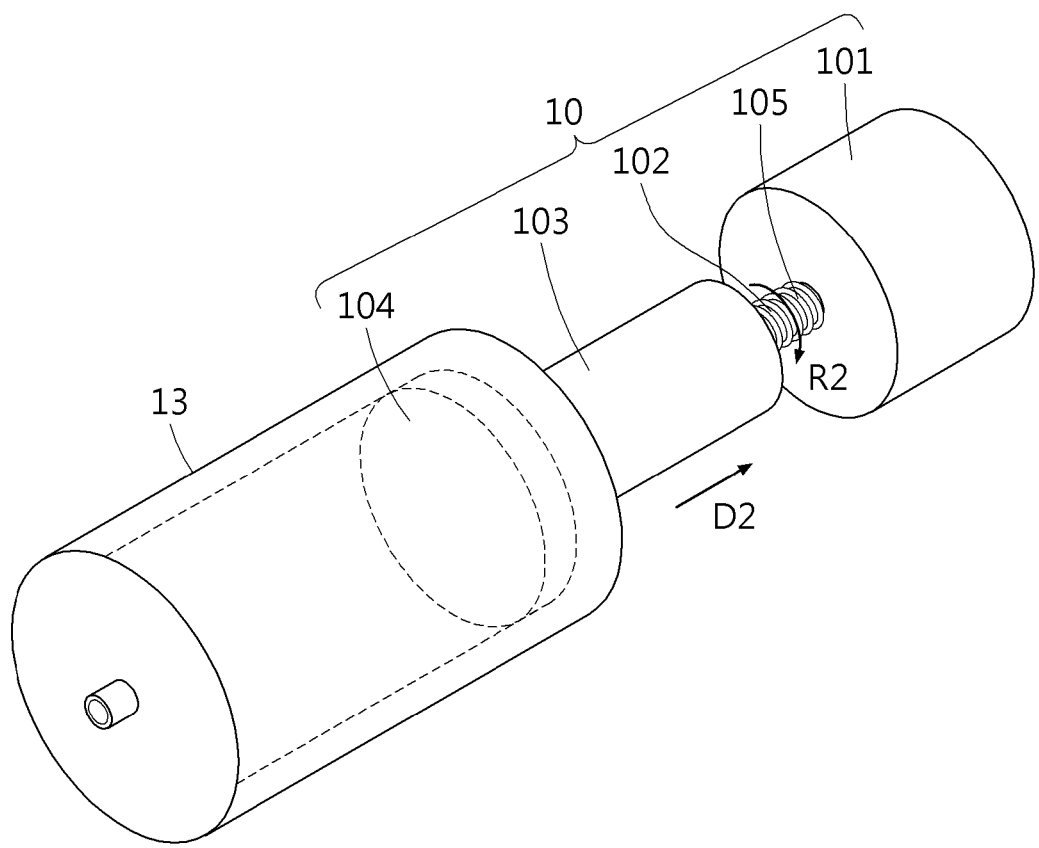
FIG. 7 is a view illustrating an example operation of a cartridge driving module according to an embodiment.

FIGS. 6 and 7 are views illustrating an example operation of a cartridge driving module according to an embodiment.

An operational process of the cartridge driving module 10 is described below with reference to FIGS. 6 and 7.

Referring to FIG. 6, when the shaft 102 rotates in the forward direction R1 as the motor 101 operates, the power transmission 103 moves forward in the direction D1 of the cartridge.

When the shaft 102 rotates from the stop position, the first thread 1023 formed on the first portion 1021 of the shaft 102 may be engaged with the second thread 1033 formed on the first insertion portion 1031 of the insertion hole.

In this case, the position maintaining unit 105 may apply an external force in the direction D1 along which the power transmission 103 moves forward, for the first engagement between the first thread 1023 and the second thread 1033.

Thereafter, the power transmission 103 is moved forward as the shaft 102 rotates in the forward direction R1, the pusher 104 connected to an end of the power transmission 103 exerts a pressure to the medicine cartridge 13 to discharge the medicine out of the medicine cartridge 13.

Referring to FIG. 7, when the shaft 102 is rotated in the backward direction R2 by the motor 101, the power transmission 103 is moved backward in the direction D2 of the motor 101.

While the power transmission 103 moves backward, the first portion 1021 having the first thread 1023 formed thereon is moved past the first insertion portion 1031 of the insertion hole to the second insertion portion 1032.

When the power transmission 103 arrives at the stop position, i.e., when the first portion 1021 of the shaft 102 is fully positioned in the second insertion portion 1032 of the insertion hole, the first thread 1023 and the second thread 1033 are disengaged from each other, so that transmission of the rotational force of the shaft 102 to the power transmission 103 is physically cut off.

During this course, the position maintaining unit 105 is compressed by the power transmission 103 to exert an elastic force in the direction D1 along which the power transmission 103 moves forward, thus preventing the power transmission 103 from being moved back further beyond the stop position by inertia and thus allowing the power transmission 103 to remain in the stop position.

Figure 8:
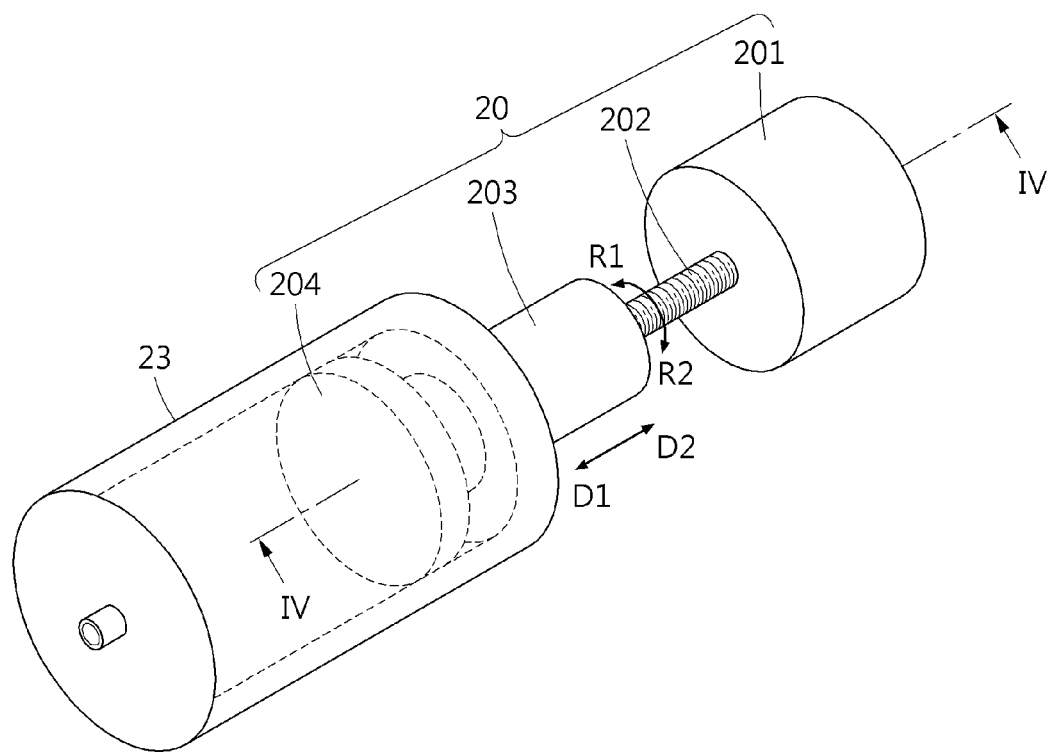
FIG. 8 is a perspective view illustrating a cartridge driving module according to an embodiment.
Figure 9:
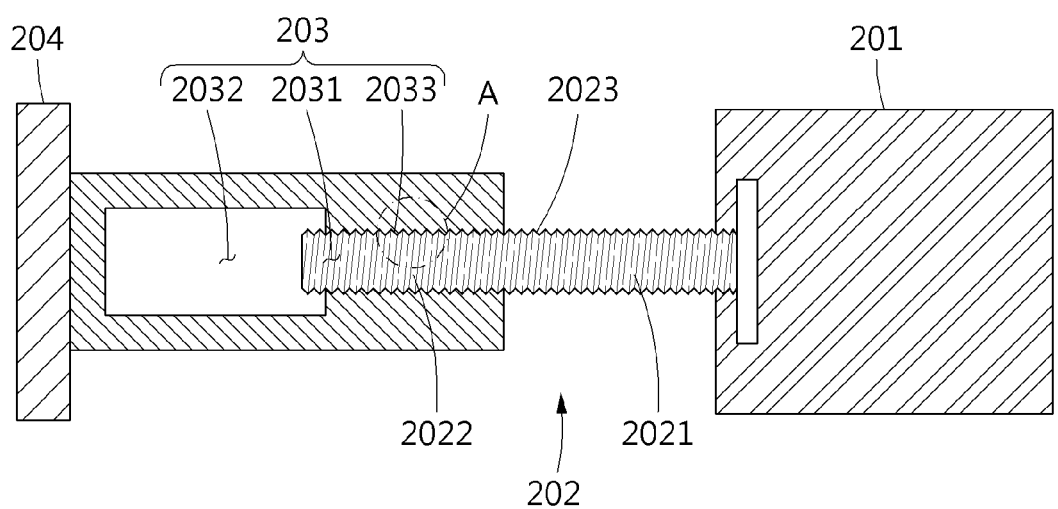
FIG. 9 is a cross-sectional view taken along line Iv-Iv of FIG. 8, according to an embodiment.

FIG. 8 is a perspective view illustrating a cartridge driving module according to an embodiment. FIG. 9 is a cross-sectional view taken along line VII-VII of FIG. 8.

Referring to FIGS. 8 and 9, according to an embodiment, a cartridge driving module 20 may include a motor 201, a shaft 202, a power transmission 203, and a pusher 204.

The shaft 202 may be connected to the motor 201 to rotate around the rotational axis of the motor 201.

The shaft 202 may be rotated in the forward direction or backward direction, or clockwise or counterclockwise, according to the operation of the motor 201.

The power transmission 203 may be connected to the shaft 202 and may be moved forwards or backwards according to the rotational direction of the shaft 202.

For example, the power transmission 203 may be moved forwards in the direction of the cartridge as the shaft 202 is rotated in the forward direction, and the power transmission 203 may be moved backwards in the direction of the motor 201 as the shaft 202 is rotated in the backward direction.

The pusher 204 may connect the power transmission 203 and the medicine cartridge 23.

When the power transmission 203 moves forward, the pusher 204 may press the medicine cartridge 23, thereby exerting a pressure to the medicine cartridge 23.

The shaft 202 and the power transmission 203 may be screwed to each other, but the shaft 202 and the power transmission 203 may be connected together not to cause locking due to the engagement therebetween.

For example, the shaft 202 may include a first thread 2023 formed on an outer surface thereof, and the power transmission 203 may include an insertion hole through which the shaft 202 is inserted and which has a second thread 2033 formed thereon to be engaged with the first thread 2023.

Thus, the shaft 202 and the power transmission 203 may be connected together via the first thread 2023 and the second thread 2033 which are engaged with each other.

The rotational force of the shaft 202 may be converted into a translation of the power transmission 203 by the engagement between the first thread 2023 and the second thread 2033. In this case, the first thread 2023 and the second thread 2033 may have the same pitch to be engaged with each other and may be shaped to be able to reduce the contact area in the engaged state so as to minimize locking due to an over-engagement therebetween.

Figure 10:
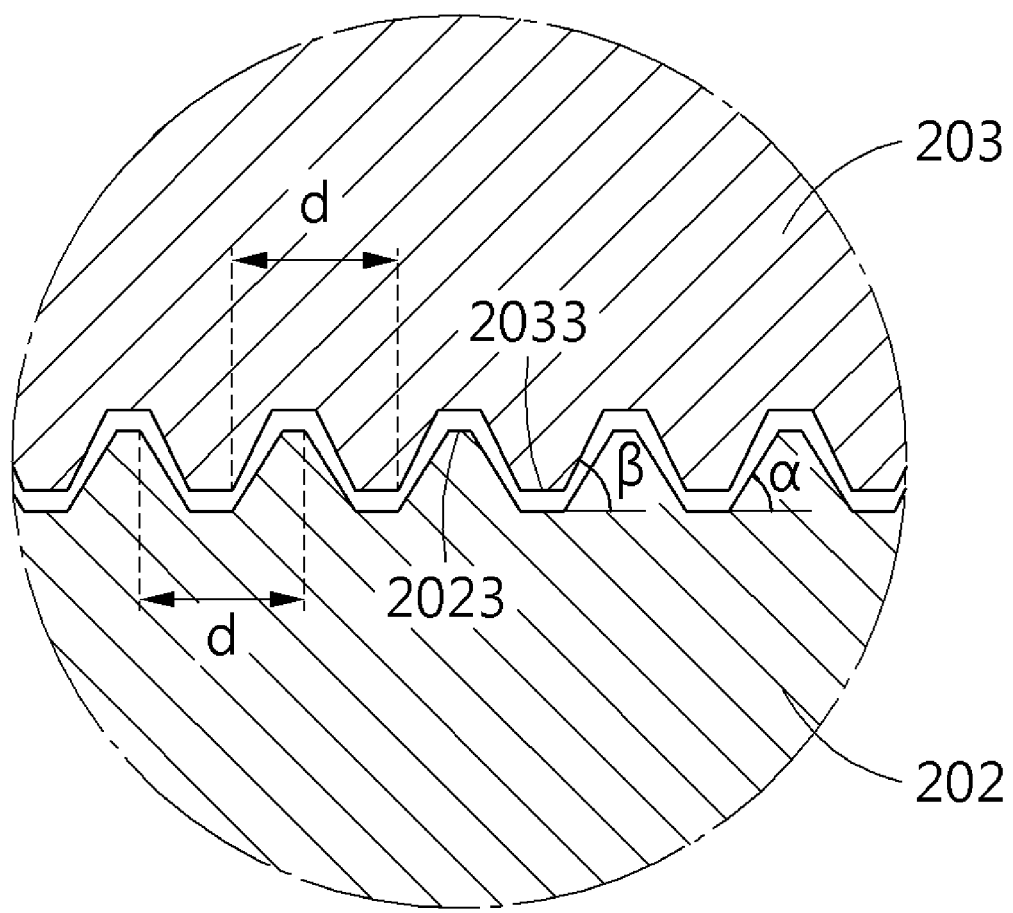
FIG. 10 is an enlarged view of portion A of FIG. 9, according to an embodiment.
Figure 11:
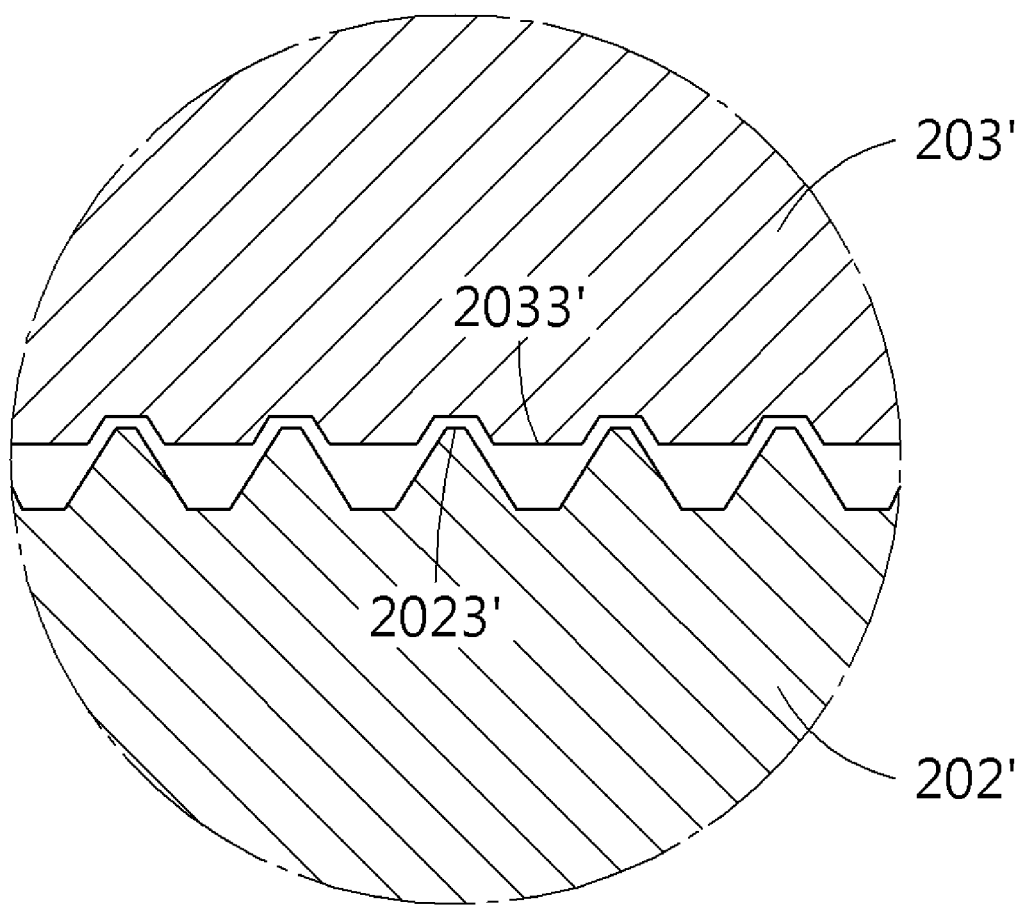
FIG. 11 is an enlarged view of portion A of FIG. 9, according to an embodiment.
Figure 12:
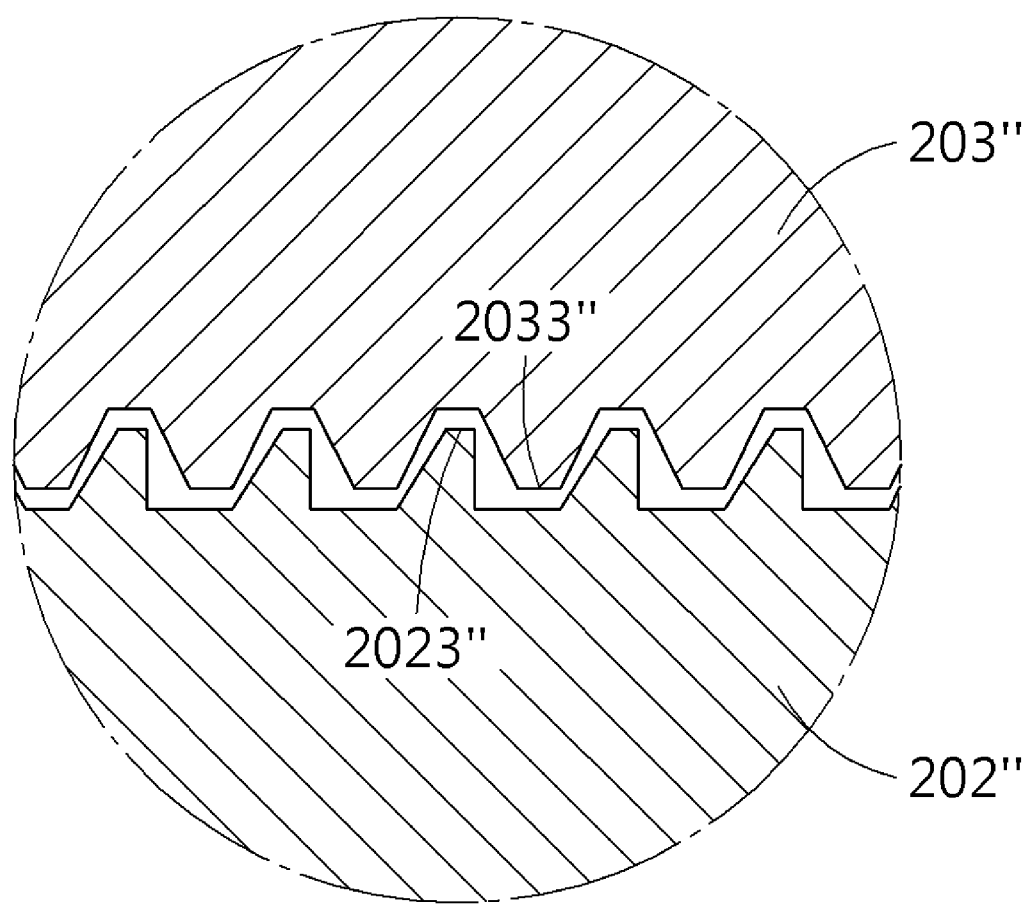
FIG. 12 is an enlarged view of portion A of FIG. 9, according to an embodiment.

FIGS. 10 to 12 are cross-sectional views of the first thread 2023 and the second thread 2033, as enlarged views of portion A of FIG. 9.

Referring to FIGS. 10 to 12, the first thread 2023 and the second thread 2033 may have the same pitch to be engaged with each other to thereby transfer power.

For example, the distance d between the plurality of crests or ridges forming the first thread 2023 may be identical to the distance d between the plurality of crests or ridges forming the second thread 2033.

Thus, as the shaft 202 rotates, the second thread 2033 may be moved along the first thread 2023, thereby allowing the power transmission 203 to translate.

The first thread 2023 and the second thread 2033 may include a structure to intentionally reduce the power transmission efficiency.

For example, the first thread 2023 and the second thread 2033 may have different flank angles as shown in FIG. 10.

For example, the thread angle of the first thread 2023 may differ from the thread angle of the second thread 2033.

In other words, the flank angle ($\alpha$) of the first thread 2023 may differ from the flank angle ($\beta$) of the second thread 2033.

In this case, since the contact area between the flanks of the first thread 2023 and the second thread 2033 is reduced in the engaged state of the first thread 2023 and the second thread 2033, the efficiency of power transmission between the first thread 2023 and the second thread 2033 may be reduced.

According to an embodiment, the first thread 2023' and the second thread 2033' may have the same pitch but different thread heights as shown in FIG. 11.

For example, as the second thread 2033' has a smaller height than the first thread 2023', transmission of power from the first thread 2023' may be reduced.

As shown in FIG. 12, the first thread 2023" and the second thread 2033" may be structured so that one of the two opposite flanks of each thread contacts the other thread but the other flank does not.

For example, each thread has pairs of flanks. When the first thread 2023 is shaped to have asymmetrical flank angles as shown in FIG. 12, the first thread 2023" and the second thread 2033" are engaged via the one-sided contact. Thus, the efficiency of power transmission may be reduced.

As such, the first thread 2023 and the second thread 2033 may have a structure to intentionally reduce the inter-flank contact area while allowing for engagement therebetween.

By such a structure, the first thread 2023 and the second thread 2033 may be prevented from over-engagement when the power transmission 203 is moved up to the position of the maximum backward movement.

Figure 13:
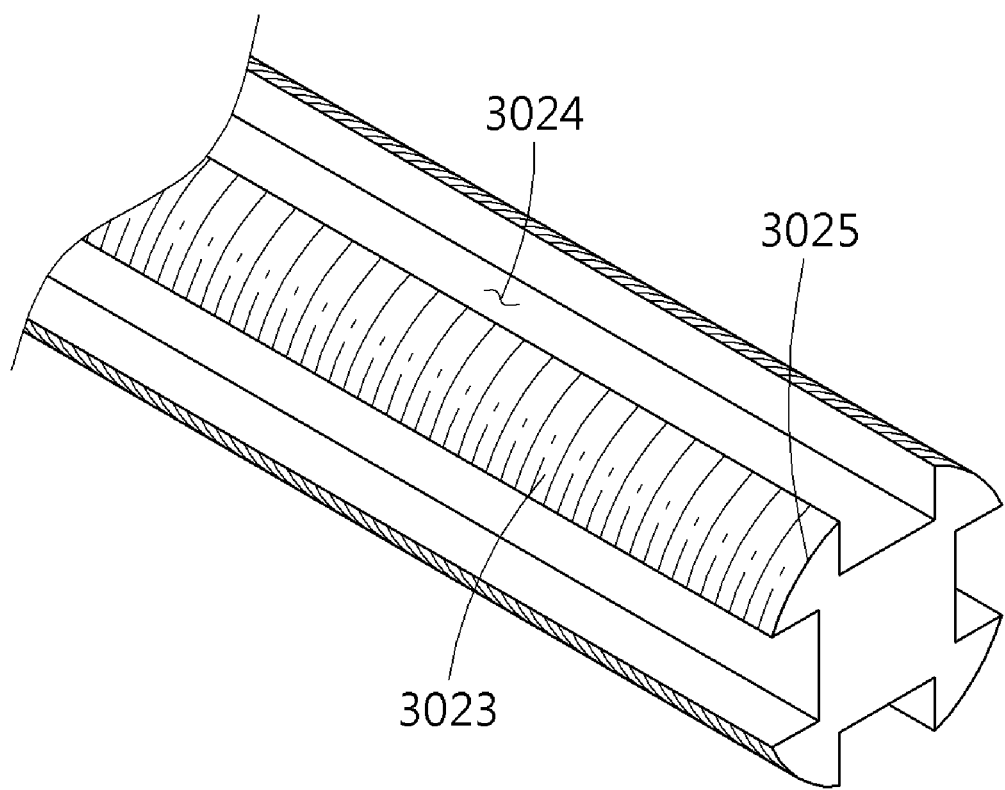
FIG. 13 is a perspective view illustrating a shaft according to an embodiment.

FIG. 13 is a perspective view illustrating a shaft 302 according to an embodiment.

Referring to FIG. 13, according to an embodiment, the shaft 302 may include a first thread 3023 formed on the outer surface to be screwed with the power transmission 203.

The shaft 302 may include a plurality of protruding surfaces 3025 protruding outwards along the circumference and a plurality of recessed surfaces 3024 depressed from the protruding surfaces 3025, with respect to the cross section perpendicular to the length direction.

The plurality of protruding surfaces 3025 and the plurality of recessed surfaces 3024 may be alternately and repetitively formed as viewed in the cross sectional view of the shaft 302.

In this case, the first thread 3023 may be formed only on the protruding surfaces 3025.

In other words, as the first thread 2023 is not formed on the recessed surfaces 3024, the contact area between the first thread 3023 and the second thread 2033 may be reduced in the engaged state between the first thread 3023 and the second thread 2033 of the power transmission 203.

Although the disclosure is shown and described in connection with embodiments, it will be easily appreciated by one of ordinary skill in the art that various changes or modifications may be made without departing from the scope of the disclosure.

For example, although the techniques described herein are performed in a different order from those described herein and/or the components of the above-described structure or device are coupled, combined, or assembled in a different form from those described herein, or some components are replaced with other components or equivalents thereof, a proper result may be achieved.

What is claimed is:

1. A cartridge driving module, comprising:
a motor and a shaft extending along a rotational axis of the motor;
a power transmission screwed to the shaft and moving forward when the shaft rotates in a forward direction and moving back when the shaft rotates in a backward direction;
a pusher connected to the power transmission and exerting a pressure to a medicine cartridge containing a medicine when the power transmission moves forward; and
a position maintaining unit exerting an external force to the power transmission in a direction along which the power transmission moves forward when the power transmission moves back up to a predetermined stop position, wherein a first thread is formed on an outer surface of the shaft, wherein the power transmission includes an insertion hole through which the shaft is inserted, wherein a second thread is formed on an inner circumferential surface of the insertion hole, and wherein the first thread is engaged with the second thread, wherein in the direction along which the power transmission moves forward, the shaft includes a first portion having a circular cross section and a second portion extending from an end of the first portion, and wherein the first thread is formed on an outer surface of the second portion, wherein in the direction along which the power transmission moves forward, the insertion hole includes a first insertion portion having a cross section corresponding to the shaft and having the second thread formed on an inner circumferential surface thereof and a second insertion portion communicating with the first insertion portion and having a larger cross section than the first insertion portion.

2. The cartridge driving module of claim 1, wherein transmission of a rotational force from the shaft is cut off when the second portion of the shaft is positioned at the second insertion portion of the insertion hole while the power transmission moves back.

3. The cartridge driving module of claim 1, wherein the predetermined stop position is a position where the first portion of the shaft is inserted to the first insertion portion of the insertion hole.

4. The cartridge driving module of claim 3, wherein when the power transmission moves back and arrives at the predetermined stop position, the position maintaining unit exerts an external force in the direction along which the power transmission moves forward to thereby keep the power transmission in position.

5. A cartridge driving module, comprising:
a motor and a shaft extending along a rotational axis of the motor;
a power transmission screwed to the shaft and moving forward when the shaft rotates in a forward direction and moving back when the shaft rotates in a backward direction;
a pusher connected to the power transmission and exerting a pressure to a medicine cartridge containing a medicine when the power transmission moves forward; and
a position maintaining unit exerting an external force to the power transmission in a direction along which the power transmission moves forward when the power transmission moves back up to a predetermined stop position, wherein the position maintaining unit includes an elastic member wound around the first portion of the shaft and compressed by the power transmission to exert an elastic force to the power transmission.

6. A medicine injection device, comprising:
a motor and a shaft connected with the motor;
a medicine cartridge containing a medicine and, when pressed, discharging the medicine to an outside;
a pusher connected with the medicine cartridge to apply a pressure to the medicine cartridge; and
a power transmission connecting the shaft and the pusher, wherein the power transmission moves forward in a direction of the medicine cartridge when the shaft rotates in a first direction and moves back in a direction of the motor when the shaft rotates in a second direction opposite to the first direction, wherein the shaft and the power transmission are screwed with each other not to be locked, wherein the shaft includes a first thread formed on an outer surface thereof, wherein the power transmission includes an insertion hole through which the shaft is inserted and a second thread formed on an inner circumferential surface of the insertion hole and engaged with the first thread, and wherein the first thread and the second thread have the same pitch and different thread angles.

7. The medicine injection device of claim 6, wherein the shaft includes a plurality of protruding surfaces protruding outward along a circumference thereof and a plurality of recessed surfaces depressed inward as viewed in a cross section view perpendicular to a length direction of the shaft.

8. The medicine injection device of claim 6, further comprising a position maintaining unit configured to maintain the power transmission in a predetermined stop position while the power transmission moves back, wherein the position maintaining unit includes an elastic member disposed between the motor and the power transmission.

9. The medicine injection device of claim 8, wherein the connection between the power transmission and the shaft is released when the power transmission arrives at the predetermined stop position.

* * * * *